United States Patent [19]

Lambert et al.

[11] 4,402,327

[45] Sep. 6, 1983

[54] EXTERNAL CARDIAC COMPRESSION ALARM SYSTEM

[76] Inventors: E. H. Lambert, 44 Gunton Dr., Lowestoft Suffolk, NR 32 4QB, England; T. A. Don Michael, 2108 Truxtun Ave., Bakersfield, Calif. 93301

[21] Appl. No.: 272,925

[22] Filed: Jun. 12, 1981

[51] Int. Cl.³ ............................................. A61B 5/00
[52] U.S. Cl. .................................... 128/774; 340/573
[58] Field of Search ........................... 128/1 D, 51-55, 128/202.28, 207.15, 344, 349 B, 672-673, 677, 748, 774, 778, 780, 782, 28; 116/266, 293; 250/338; 340/573, 688

[56] References Cited

U.S. PATENT DOCUMENTS

| | | | |
|---|---|---|---|
| 923,303 | 1/1909 | Shults | 128/344 |
| 2,396,351 | 3/1946 | Thompson | 128/748 |
| 2,979,628 | 4/1961 | Gaon | 340/688 X |
| 3,441,740 | 4/1969 | De Cloux et al. | 340/688 X |
| 3,965,355 | 6/1976 | Maccabee et al. | 250/338 X |
| 4,050,449 | 9/1977 | Castellana et al. | 128/778 |
| 4,059,099 | 11/1977 | Davis | 128/51 X |
| 4,106,002 | 8/1978 | Hogue, Jr. | 340/573 X |

*Primary Examiner*—Lee S. Cohen
*Assistant Examiner*—Christine A. Fukushima
*Attorney, Agent, or Firm*—Spensley, Horn, Jubas & Lubitz

[57] ABSTRACT

An external cardiac compression alarm system is disclosed comprising an inflatable balloon which may be inserted through the esophagus into the chest region of a patient undergoing cardiac arrest, said balloon being connected by a tube to a pressure gauge. The pressure gauge, in turn, is connected to a speaker which may emit two tones. There are two switches provided on the pressure gauge, one switch corresponding to a desired minimum degree of pressure to be exerted on the patient and the second switch corresponding to a desired maximum degree of pressure such that when the first switch is activated by the pressure gauge, the speaker emits one tone and when the second switch is activated, the speaker emits a second tone, thereby providing both audio and visual feedback immediately to a person performing external cardiac compression.

7 Claims, 2 Drawing Figures

EXTERNAL CARDIAC COMPRESSION ALARM SYSTEM

BACKGROUND OF THE INVENTION

1. Field of the Invention

This invention relates to cardiopulmonary resuscitation, and more particularly, to a device for measuring the force exerted during external cardiac compression.

2. Prior Art

Many lives are saved each year by the administration of cardiopulmonary resuscitation (CPR) to heart attack victims. However, such CPR is not foolproof. Frequently, the force exerted on the victim's chest during CPR is either substantially more than necessary or substantially less than necessary. When too great a force is used, the result can be broken ribs or other damage to the chest area. When too little force is used, the resuscitation efforts may be unsuccessful. Clearly, avoidance of either of these results is desired.

There are no devices presently known which provide an effective and efficient means for measuring the amount of pressure exerted on the chest of a patient during external cardiac compression. Thus, the person administering the aid can only guess whether or not he is exerting the proper amount of force.

There are devices which provide audio and visual feedback for use with a mannequin. Such mannequins are used for practicing the technique of CPR and for teaching unskilled persons how to administer CPR. However, these prior art devices are wired directly to the mannequin's sternum. They are not practical for use with a human being undergoing cardiac arrest. Thus, the only method currently available for teaching the appropriate amount of pressure to be exerted during CPR is to have a person practice on a mannequin with such a device. The person will then get an approximate feel of the proper force to be applied. This method does not provide any feedback while CPR is actually being performed on a live patient. It cannot be used with a live patient to provide such feedback, which can often be the difference between life and death.

BRIEF SUMMARY OF THE INVENTION

It is therefore an object of this invention to provide a device for measuring the pressure exerted on the chest of a heart attack patient during the administration of cardiopulmonary resuscitation.

It is another object of this invention to provide a device as described above which provides both audio and visual feedback to indicate the appropriate pressures.

It is a further object of this invention to provide a device as described above which is easily inserted into the patient's chest area.

Pursuant to the present invention, there is provided an intra-thoracic or esophageal inflatable balloon. The balloon is inserted through the esophagus into the chest area of the patient and is connected to a tube which extends out the mouth of the patient.

The tube is connected to an audio visual alarm system. This system comprises a pressure gauge to measure the pressure exerted on the inflated balloon and a speaker connected to the pressure gauge. The dial of the pressure gauge is connected to the speaker so that at a predetermined minimum pressure, the dial will activate one tone through the speaker. At a predetermined maximum pressure, the dial will activate a second tone through the speaker.

In operation, when force is exerted on the patient's chest, the air in the balloon is compressed. This compression is transmitted via the tube to the pressure gauge. When the needle on the pressure gauge passes a certain minimum predetermined pressure, one tone will be emitted by the speaker. This minimum corresponds to the minimum force necessary for the efficacy of the resuscitation.

When further force is exerted on the chest of the patient, the needle on the gauge will pass a second position corresponding to the maximum pressure desired so that damage is not done to the patient's chest area. When the needle passes this second position, a second tone will be emitted by the speaker.

Therefore, the person administering the CPR may either visually watch the dial of the pressure gauge to determine the force that he is exerting or may listen for the tones emitted by the speaker which will indicate when the minimum level is passed and when the maximum level is passed. Thus, pressure in the disired range may be exerted consistently and without the danger of the exertion of too little or too much pressure.

The novel features which are believed to be characteristic of the invention, both as to its configuration and method of operation, together with further objectives and advantages thereof, will be better understood from the following description considered in connection with the accompanying drawings in which a presently preferred embodiment of the invention is illustrated by way of example. It is to be expressly understood, however, that the drawings are for the purpose of illustration and description only, and are not intended as a definition of the limits of the invention.

DETAILED DESCRIPTION OF THE PREFERRED EMBODIMENT

Figure 1:
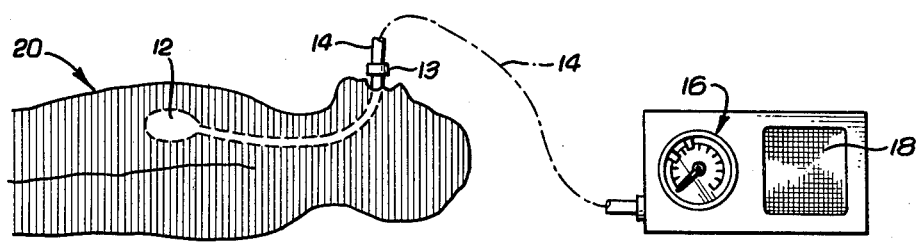
FIG. 1 is a schematic view of the external cardiac compression alarm system of the present invention.

Referring first to FIG. 1, there is shown a schematic representation of the external cardiac compression alarm system 10 of the present invention. The system 10 of the present invention generally comprises an intrathoracic or esophageal inflatable balloon 12 which is connected to a tube 14 which in turn is connected to a pressure gauge 16 through a non return valve 13. Connected to the pressure gauge 16 is a speaker 18 which is capable of emitting two tones.

The balloon 12 is inserted in the esophagus of the patient 20 so that the balloon 12 is situated below the chest region where the external cardiac compression is to be applied and inflated by a syringe through a non return valve 13.

Figure 2:
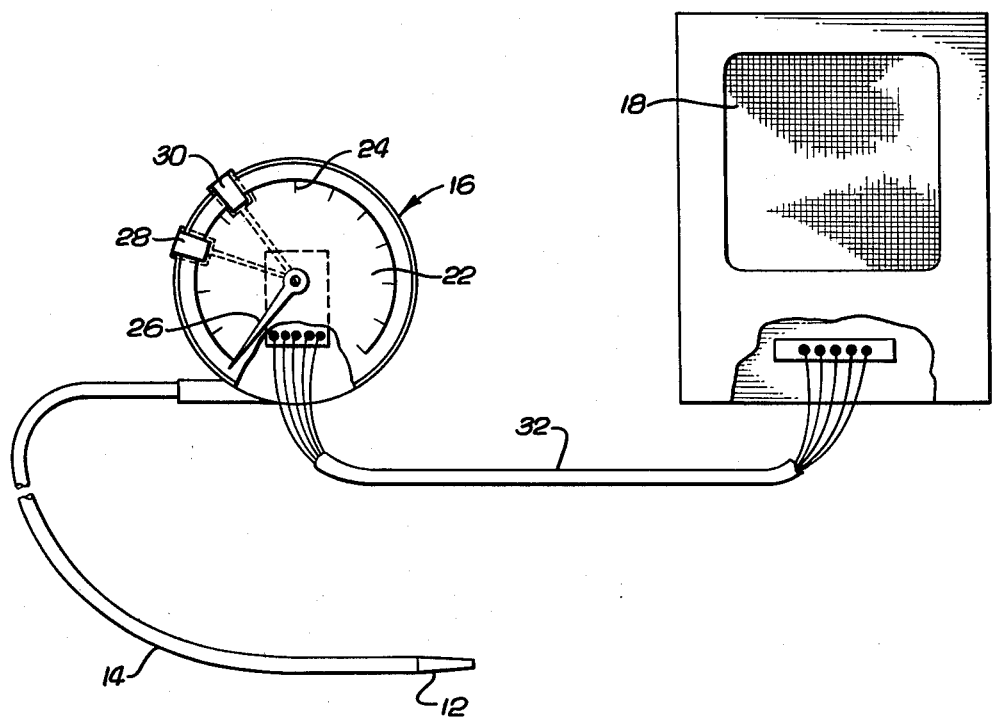
FIG. 2 is an elevational view of the various components of the system of the present invention.

Referring next to FIG. 2, one can see the detailed aspects of a preferred embodiment for the pressure gauge 16 and the speaker 18 of the present invention. The pressure gauge 16 is provided with a dial 22 which has calibrations 24 in millimeters of mercury. When external cardiac compression is performed, the pressure in the balloon 12 will increase and be transmitted via the tube 14 to the pressure gauge 16. As the pressure in the balloon 12 increases, the needle 26 of the gauge 16 will rotate in a clockwise direction.

At preselected points on the dial 22, there are placed a first infrared switch 28 and a second infrared switch 30. Such infrared switches 28 and 30 are well known in the art and comprise an infrared beam, which, when interrupted, will cause a signal to be generated. These switches 28 and 30 may be moved to correspond to any desired pressures recordable by the gauge 16. The first infrared switch 28 is placed at an appropriate pressure such that it is desired that each compression be of such force to provide at least such minimum pressure. Thus, when the needle 26 passes through an infrared beam in the first infrared switch 28, the first infrared switch 28 will be activated. This activation will be communicated to the speaker 18 by means of cable 32, causing the speaker to emit a first tone. This first tone will alert the user that the minimum pressure has been achieved.

The second infrared switch 30 should then be placed at a point on the dial 22 corresponding to the maximum pressure desired to be applied. Thus, if the needle 26 continues in a clockwise direction so that it activates the second infrared switch 30, this activation will be relayed to the speaker 18, causing the speaker 18 to emit a second tone. This second tone indicates to the user that too much force has been applied.

Thus, it can be seen that under the present invention, the user can immediately determine both visually by viewing the needle 26 on the pressure gauge 16 and aurally, by hearing the two different tones emitted by the speaker 18, whether or not he has used an appropriate amount of pressure in performing external cardiac compression. By setting the switches 28 and 30 at appropriate levels such that the infrared circuit is interrupted at the desired pressures, an audio visual signal is provided both at static pressures as well as dynamic pressures during actual external cardiac compression.

While a wide variety of materials, shapes and other configurations can be used in this invention, it should be understood that changes can be made without departing from the spirit or scope thereof. This invention, therefore, is not to be limited to the specific embodiments discussed and illustrated herein.

We claim:

1. A cardiac compression alarm system for insertion through the mouth and esophagus to a position adjacent the chest region, comprising:

sensor means configured to be inserted through the mouth and esophagus into the chest region of a person for sensing changes in external pressure applied to said chest region;

a conduit joined to said sensor means, said conduit of sufficient length so as to extend from the sensor means through the esophagus and mouth to a position external to the person;

measuring means, joined to said conduit, for measuring a change in the force exerted on said sensor means in said chest region; and indicating means, joined to said measuring means, for indicating the change in the force measured by said measuring means.

2. A system according to claim 1 wherein said measuring means comprises a pressure gauge.

3. A system according to claim 1 wherein said sensor means comprises an inflatable balloon.

4. A system according to claim 1 wherein said indicating means comprises a dial connected to said measuring means and a speaker capable of emitting first and second tones, said speaker being electrically connected to said measuring means so that when said measuring means registers a first amount of pressure, said speaker will emit said first tone, and when said measuring means registers a second amount of pressure, said speaker will emit said second tone.

5. A system accoring to claim 4, further comprising a first switching means for activating said first tone and a second switching means for activating said second tone.

6. A system according to claim 5, wherein said dial further includes a needle and said first and second switching means are activated by the passage therethrough of said needle on said dial.

7. A method for determining changes in external pressure applied to the cardiac region, such as during cardiopulmonary resuscitation, comprising the steps of:
(a) providing a compression alarm system, said compression alarm system comprising:
  (i) sensor means configured to be inserted through the mouth and esophagus into the chest region of a person for sensing changes in external pressure applied to said chest region;
  (ii) a conduit joined to said sensor means, said conduit of sufficient length so as to extend from the sensor means through the esophagus and mouth to a position external to the person;
  (iii) measuring means, joined to said conduit, for measuring a change in the force exerted on said sensor means in said chest region; and
  (iv) indicating means, joined to said measuring means, for indicating the change in the force measured by said measuring means;
(b) inserting said sensor means and said conduit through the mouth and esophagus such that the sensor means is place in said chest region;
(c) applying an external pressure to said cardiac region, whereby said measuring means measures the changes in the force exerted on said chest region and the changes are indicated on said indicating means.

* * * * *